United States Patent [19]

Marx et al.

[11] Patent Number: 4,907,444
[45] Date of Patent: Mar. 13, 1990

[54] FIRE FIGHTING FOAM ANALYZER AND METHOD THEREFOR

[75] Inventors: Martin J. Marx, 5560 Marcliffe Ave., Boise, Id. 83704; Mark A. Harper; Todd D. Halter, both of Boise, Id.

[73] Assignee: Martin Marx, Boise, Id.

[21] Appl. No.: 276,224

[22] Filed: Nov. 25, 1988

[51] Int. Cl.⁴ ............................................. G01N 33/00
[52] U.S. Cl. ..................................................... 73/60.1
[58] Field of Search ........................ 73/60.1, 53, 865.8, 73/866

[56] References Cited

U.S. PATENT DOCUMENTS

| | | | |
|---|---|---|---|
| 2,380,679 | 7/1945 | Smith | 73/60.1 |
| 3,555,885 | 1/1971 | Morales | 73/866 |
| 4,084,426 | 4/1978 | Gales | 73/60.1 |

FOREIGN PATENT DOCUMENTS

| | | | |
|---|---|---|---|
| 0127138 | 5/1959 | U.S.S.R. | 73/60.1 |
| 0650636 | 3/1979 | U.S.S.R. | 73/60.1 |
| 2158574 | 11/1985 | United Kingdom | 73/60.1 |

Primary Examiner—Robert R. Raevis
Attorney, Agent, or Firm—Frank J. Dykas; Craig M. Korfanta

[57] ABSTRACT

A method and apparatus for classifying fire fighting foam is disclosed. Fire fighting foam analyzer 10 uses a large capacity container 11 having a viewing window 12 disposed in a substantially vertical wall 13. The viewing window 12 has thereon a volume scale 14 containing volume graduations and a ratio scale 15. To classify a foam by a foam type, fire fighting foam analyzer 10 is filled with an initial volume of foam, the initial volume is recorded, solution is allowed to separate from the foam for a given period of time, a final solution volume is recorded, the ratio of initial foam volume to final solution volume is determined and the ratio is correlated to a particular foam type by reading the ratio scale 15.

5 Claims, 5 Drawing Sheets

| FOAM TYPE | RATIO RANGE |
|---|---|
| 1 | 23.5 AND UP |
| 2 | 10.5 TO 23.5 |
| 3 | 12 TO 16.5 |
| 4 | 9.3 TO 12 |
| 5 | 9.3 AND BELOW |

FIG. 5

| FOAM TYPE | RATIO RANGE |
|---|---|
| 1 | 22 AND UP |
| 2 | 14.8 TO 22 |
| 3 | 11 TO 14.6 |
| 4 | 8.8 TO 11 |
| 5 | 8.8 AND BELOW |

FIG. 6

FIRE FIGHTING FOAM ANALYZER AND METHOD THEREFOR

BACKGROUND OF THE INVENTION

1. Technical Field

This invention generally relates to apparati and methods for analyzing foam, and in particular, to a method and apparatus for analyzing and characterizing fire fighting foam.

2. Background Art

Fire fighting foam has become the method of choice in fighting and extinguishing fires. Foam, for fighting fire, has heretofore been classified very qualitatively, typically by its visual appearance and apparent viscosity. Foam has been divided into five foam types which are: Type 1, refering to a mostly air very dry and fluffy foam; Type 2, refering to a shaving cream consistency which holds peaks and does not immediately run off of a vertical surface; Type 3, refering to a watery shaving cream consistency where the peaks collapse and the foam will not hold on a vertical surface; Type 4, refering to a very wet foam which readily runs off of vertical surfaces; and Type 5, which refers to a mostly water foam which has no body at all. Obviously, this classification system leaves a lot to be desired.

Knowing the foam type is of critical importance, in that different foam types are required depending upon the fuel type of the fire. If a less expensive foam type will adequately extinguish the fire, undue expense can be incurred by using an unnecessarily thick foam.

The three widely accepted techniques for producing fire fighting foam are the water expansion pumping system (WEPS), the compressed air foam system (CAFS), and the free fall foam system (FFFS). Unfortunately, fire fighting foam type, whether produced by the WEPS, the CAFS, or the FFFS, is dependent upon four factors. The first factor is the percent concentration of the foaming agent or surfactant, the second factor is the number of gallons of water per minute expended, the third factor is the cubic feet of air per minute expended, and the fourth factor is the type of equipment, i.e., manifolds, hose dimensions, nozzles, etc. The first three of these factors, i.e. the foaming agent, water and air concentrations, are heavily dependent upon the fourth factor, the equipment type and settings.

Prior to the present invention, foam analysis was accomplished by measuring the foam conductivity or solution drainage rate. A device which measures solution drainage rate is taught by GALES, U.S. Pat. No. 4,084,426. Gales teaches a test tube having a plurality of light emitting diode and phototransistor pairs located at opposing sides of the test tube along its entire length. Digital circuitry successively scans the LED and phototransistor array to determine the point at which the foam and solution interface is located and calculates a drainage/dissipation rate using successive scans. Unfortunately, as will be explained, dissipation rate is not indicative of fire fighting foam type. Hence, the Gales device is unsuitable for classifying fire fighting foam by type.

Recently, there has been a substantial amount of interest in using fire fighting foam on structure fires as well as open range and forest fires. In fighting range and forest fires, water is obviously scarce and in high demand. Accordingly, a fire fighter must determine the foam type necessary to extinguish a particular fire, depending upon the fuel type, considering also the availability of water, number of trips necessary to lay the required foam line, time and progress lost in successive trips and the cost of the foaming agent, e.g. surfactant. In fighting structure fires, on the other hand, scarcity of water is normally not the overriding consideration. Instead the fire fighter must balance the cost of water damage against damages incurred as a result of a slowly extinguished fire.

Typically, water damage far exceeds the actual fire damage. Very few fire stations are equipped with foam generating equipment, simply because highly skilled personnel have heretofore been required to produce the proper foam type for any given fire. In fact, present day foam making is more of an art than a science.

Therefore, what is needed is a fire fighting foam analyzing method and apparatus which requires a minimum amount of skill to accurately characterize foam so that any given piece of foam generating equipment can be calibrated and optimized to produce the necessary foam type.

DISCLOSURE OF INVENTION

As was previously discussed, foam has heretofore been analyzed by measuring conductivity and/or drainage rates. It has been found, through experimentation, that, given a particular piece of foam generating equipment, simply raising the surfactant concentration, keeping all other contributing components constant, will in fact result in a lower number classification of foam, i.e. a dryer foam. However, given two pieces of identical equipment, except for the diameter of delivery hoses, for example, identical surfactant concentrations will result in the two machines producing two distinctive foam types. Similarly, different manifolds or nozzles yields yet different results.

This is simply a consequence of the different scrubbing actions experienced in the two different equipment configurations. Since the two foams were produced from identical concentrations of surfactant, they will demonstrate similar surface tensions and therefore, similar drainage rates, even though the two foams are completely different types. This is thought to be the reason why drainage rates are not indicative of foam type. Analyzing fire fighting foam using conventional conductivity and dissipation rate analysis proved to be totally inaccurate in classifying the foam types.

The inventors of the present invention, through extensive research, have demonstrated that at certain times after the initial preparation, there exist very predictable ratios of initial foam volume to final solution volume, which are indicative of the foam type. Therefore, the foam can be predicted regardless of the equipment settings and configuration.

Using these time dependent ratios, a fire fighter can determine the type of foam produced by the settings of his particular equipment configuration simply and quickly by measuring an initial foam volume, a final solution volume, determining the ratio of foam to solution volumes and comparing this ratio to the already empirically determined ratios.

It is therefore an object of the present invention to provide an apparatus and method, as previously described, for evaluating the type of foam produced by a particular equipment configuration.

This object is accomplished by a large capacity container, typically in excess of sixty gallons, having a window disposed in a vertical side which contains volume graduations for measuring the initial foam level and final solution level. The window also contains a second scale for correlating an initial foam to final solution ratio with a particular foam type.

BRIEF DESCRIPTION OF THE DRAWINGS

FIG. 5 is a thirty minute correlation chart.

FIG. 6 is a sixty minute correlation chart.

BEST MODE FOR CARRYING OUT INVENTION

Figure 1:
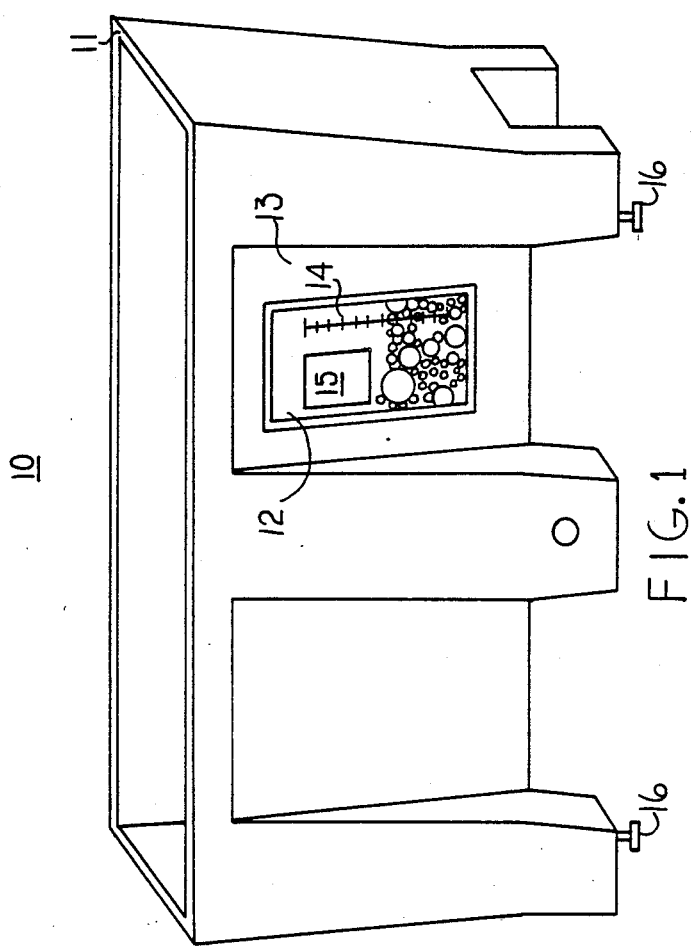
FIG. 1 is a perspective representational view of a fire fighting foam analyzer.
Figure 2:
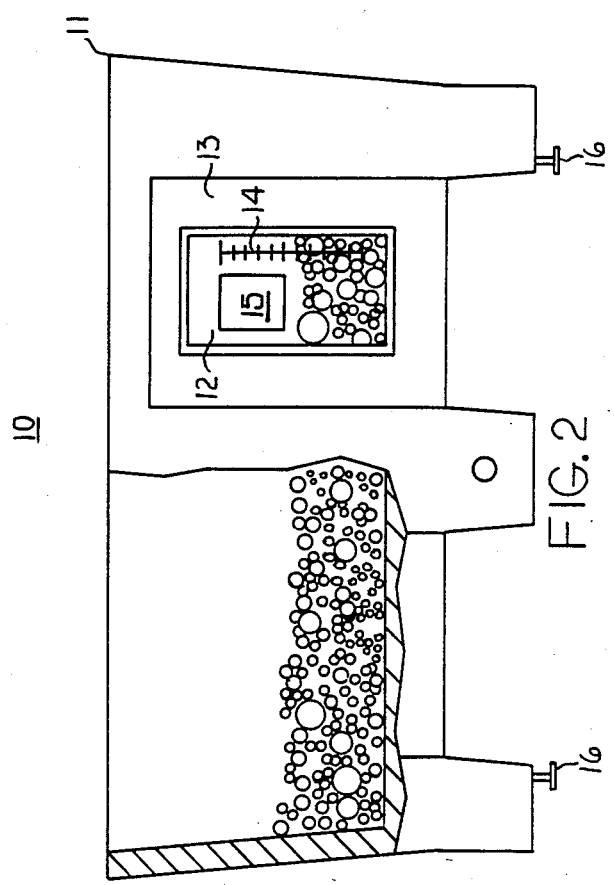
FIG. 2 is a front side sectional view of a fire fighting foam analyzer.
Figure 3:
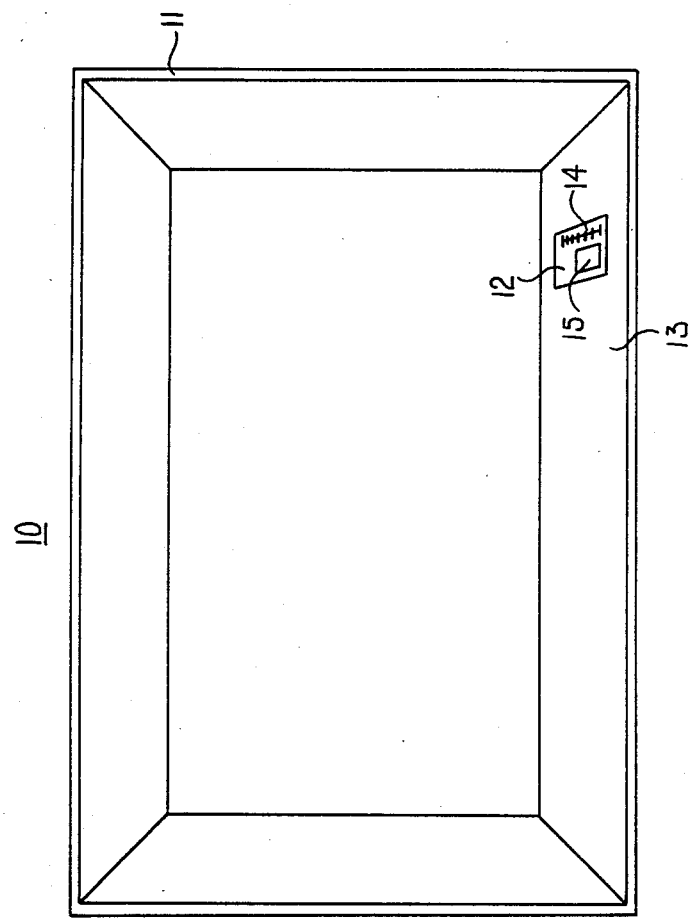
FIG. 3 is a top plan view of a fire fighting foam analyzer.

Referring now to FIGS. 1 through 3, fire fighting foam analyzer 10, also referred to FF analyzer 10, is shown. FF analyzer 10 generally has a large capacity container 11 supported by leveler legs 16. A window 12 is provided in a substantially vertical wall 13 and has a first indicia means, volume scale 14 and a second indicia means, ratio to foam type correlating indicia 15, thereon. Ratio to foam type correlating indicia 15 consists of the information contained within chart 23 and/or chart 24 as are shown in FIGS. 5 and 6 respectively. As can be seen in FIG. 2, the graduations of volume scale 14 correspond to a specific volume level contained within large capacity container 11.

Figure 4:
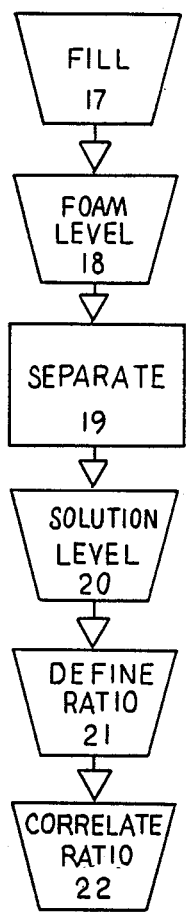
FIG. 4 is a flow chart depicting the method steps of classifying fire fighting foam.

Referring also now to FIG. 4, the method steps for classifying fire fighting foam are depicted. The first step, 17, is to fill FF analyzer 10 with fire fighting foam. The second step, 18, is to measure and record an initial foam volume level. The third step, 19, is to allow solution to separate from the foam for one of the two given time periods, i.e. either thirty minutes or sixty minutes. The fourth step, 20, is to measure and record a final solution volume level. The fifth step, 21, is to define an initial foam volume to final solution volume ratio which is determined by dividing the initial foam volume level by the final solution volume level. The sixth and final step, 22, is to correlate the defined ratio with a given foam type using either the thirty minute correlation chart 23, shown in FIG. 5, or the sixty minute correlation chart 24, shown in FIG. 6. It should be noted that by the end of the sixty minute period, essentially all the foam has dissipated into solution and the final solution level may be obtained at any time after the sixty minute separation period. Of course, evaporation rates must be taken into account should the final solution level be taken at some extended time period after the initial sixty minute separation period.

The present invention allows a fire fighter a simple method for determining the proper settings and equipment configuration for producing different foam types. The proper settings and configurations can be conveniently determined in the parking lot of the fire house at the fire fighter's leisure. Once the fire fighter has determined which settings produce which foam types, he can set the equipment accordingly, depending upon the fuel type of the fire.

While there is shown and described the present preferred embodiment of the invention, it is to be distinctly understood that this invention is not limited thereto but may be variously embodied to practice within the scope of the following claims.

We claim:

1. A fire fighting foam analyzer which comprises:
   a multi-gallon capacity container of known volume having at least one vertical wall, for receiving fire fighting foam and determining initial foam to final solution ratios; and
   a transparent window disposed in said wall having a first visual indicia means thereon defining volume graduations for indicating the volumes of the initial foam and final solution within said multi-gallon capacity container at any particular level and further having a ratio to foam type correlating indicia thereon for correlating an initial foam to final solution ratio to a particular fire fighting foam type.

2. A method of classifying fire fighting foam by type using the analyzer of claim 1, comprising the steps of:
   1. filling said fire fighting foam analyzer with fire fighting foam;
   2. reading first said visual indicia means to obtain an intial foam volume;
   3. allowing solution to separate from the foam for a specified period of time;
   4. reading said first visual indicia means to obtain a final solution volume;
   5. defining a foam to solution ratio which is equal to the initial foam volume divided by the final solution volume; and
   6. classifying the foam type using said ratio to foam type correlating indicia to correlate the foam to solution ratio to a specific foam type.

3. A method of classifying fire fighting foam by type using a multi-gallon capacity container of known volume having at least one generally vertical wall, for receiving fire fighting foam and determining initial foam to final solution ratios and a transparent window disposed in the wall having a first visual indicia means thereon defining volume graduations for indicating the volumes of the initial foam and final solution within said multi-gallon capacity container at any particular level, comprising the steps of:
   1. filling said fire fighting foam analyzer with fire fighting foam;
   2. reading said first visual indicia means to obtain an initial foam volume;
   3. allowing solution to separate from the foam for a specified period of time;
   4. reading said first visual indicia means to obtain a final solution volume;
   5. defining a foam to solution ratio which is equal to the initial foam volume divided by the final solution volume; and
   6. classifying the foam type by correlating the foam to solution ratio to a corresponding foam type.

4. A method for classifying fire fighting foam by type, comprising the steps of:
   1. filling a container with a known volume of fire fighting foam;
   2. allowing solution to separate from the foam for thirty minutes;
   3. measuring the volume of the separated solution;
   4. determining the ratio of foam to separated solution; and
   5. identifying the foam type which corresponds to the determined ratio using the following chart:

| FOAM TYPE | RATIO RANGE |
|---|---|
| 1 | 23.5 and up |
| 2 | 16.5 to 23.5 |
| 3 | 12 to 16.5 |
| 4 | 9.3 to 12 |
| 5 | 9.3 and below |

5. A method for classifying fire fighting foam by type, comprising the steps of:
1. filling a container with a known volume of fire fighting foam;
2. allowing solution to separate from the foam for sixty minutes;
3. measuring the volume of the separated solution;
4. determining the ratio of foam to separated solution; and
5. identifying the foam type which corresponds to the determined ratio using the following chart:

| FOAM TYPE | RATIO RANGE |
|---|---|
| 1 | 22 and up |
| 2 | 14.6 to 22 |
| 3 | 11 to 14.6 |
| 4 | 8.8 to 11 |
| 5 | 8.8 and below |

* * * * *